United States Patent
Panian et al.

(10) Patent No.: US 9,067,049 B2
(45) Date of Patent: Jun. 30, 2015

(54) PROVIDING POSITIVE DISPLACEMENT UPON DISCONNECTION USING A CONNECTOR WITH A DUAL DIAPHRAGM VALVE

(75) Inventors: Tyler Devin Panian, Long Beach, CA (US); George Mansour, Pomona, CA (US)

(73) Assignee: CAREFUSION 303, INC., San Diego, CA (US)

( * ) Notice: Subject to any disclaimer, the term of this patent is extended or adjusted under 35 U.S.C. 154(b) by 931 days.

(21) Appl. No.: 13/190,346

(22) Filed: Jul. 25, 2011

(65) Prior Publication Data

US 2013/0030386 A1  Jan. 31, 2013

(51) Int. Cl.
A61M 39/26 (2006.01)
F16L 37/40 (2006.01)
A61M 39/22 (2006.01)

(52) U.S. Cl.
CPC ........... *A61M 39/22* (2013.01); *Y10T 29/49405* (2015.01); *F16L 37/40* (2013.01); *A61M 2039/263* (2013.01); *A61M 2039/266* (2013.01); *A61M 2039/261* (2013.01)

(58) Field of Classification Search
USPC ............... 251/149.6, 149.7; 604/167.03, 246, 604/249, 533, 537, 539, 536
See application file for complete search history.

(56) References Cited

U.S. PATENT DOCUMENTS

| | | | |
|---|---|---|---|
| 5,730,418 A | 3/1998 | Feith et al. | |
| 6,228,069 B1 * | 5/2001 | Barth et al. | 604/249 |
| 6,482,188 B1 * | 11/2002 | Rogers et al. | 604/249 |
| 7,014,169 B2 * | 3/2006 | Newton et al. | 251/149.6 |
| 7,520,489 B2 * | 4/2009 | Ruschke et al. | 251/149.7 |
| 2006/0163515 A1 | 7/2006 | Ruschke | |
| 2009/0184275 A1 * | 7/2009 | Ruschke et al. | 251/149.1 |
| 2010/0059702 A1 | 3/2010 | Mansour et al. | |
| 2010/0217208 A1 * | 8/2010 | Snow | 604/246 |
| 2011/0028914 A1 | 2/2011 | Mansour et al. | |
| 2011/0130724 A1 | 6/2011 | Mansour et al. | |

FOREIGN PATENT DOCUMENTS

WO  2011060384 A1  5/2011

OTHER PUBLICATIONS

International Search Report and Written Opinion for PCT/US2012/047078 mailed Jan. 25, 2013.

* cited by examiner

*Primary Examiner* — John K Fristoe, Jr.
*Assistant Examiner* — Jonathan Waddy
(74) *Attorney, Agent, or Firm* — McDermott Will & Emery LLP

(57) ABSTRACT

Positive displacement using a connector with dual diaphragms is provided. For example, the connector includes a single fluid flow path, an air chamber and a valve. The single fluid flow path is configured for delivering fluid to a person and configured for receiving fluid from a person. The air chamber configured for expelling air from the air chamber when an actuator is inserted into the connector and for receiving air into the chamber when the actuator is removed from the connector. The valve plug comprises two diaphragms that separate the air chamber from the single fluid flow path. The valve plug is configured for creating positive displacement by returning the valve plug to its uncompressed state when the actuator is removed from the connector.

37 Claims, 15 Drawing Sheets

```
                    ┌─────────────────────────────────────────────────┐
                    │ AN INSERT IS SECURELY CONNECTED WITH A BASE     │
                    │                      822                        │
                    └─────────────────────────────────────────────────┘
                                          │
                                          ▼
                    ┌─────────────────────────────────────────────────┐
                    │ A VALVE PLUG THAT INCLUDES TWO DIAPHRAGMS IS INSERTED │
                    │                      824                        │
                    └─────────────────────────────────────────────────┘
                                          │
                                          ▼
                    ┌─────────────────────────────────────────────────┐
                    │ A HOUSING IS PLACED OVER THE VALVE PLUG AND THE INSERT │
                    │                      826                        │
                    └─────────────────────────────────────────────────┘
                                          │
                                          ▼
                    ┌─────────────────────────────────────────────────┐
                    │ THE HOUSING IS SECURELY CONNECTED WITH THE BASE │
                    │                      828                        │
                    └─────────────────────────────────────────────────┘
```

FIG. 8B

PROVIDING POSITIVE DISPLACEMENT UPON DISCONNECTION USING A CONNECTOR WITH A DUAL DIAPHRAGM VALVE

FIELD OF THE INVENTION

The present technology relates generally to medical connectors. More particularly, the present technology relates to providing positive displacement upon disconnection of an actuator from a connector by using a connector with a dual diaphragm valve.

BACKGROUND

Medical connectors are widely used for delivering fluid to a patient or for drawing fluid from a patient. Examples of delivered fluid include, but are not limited to, medication, intravenous fluid and enteral feeding fluid. Examples of fluids that are drawn from a patient include blood and bodily fluids.

The use of hypodermic needles has been gradually decreasing due to the risks of infection and cost considerations, among other things. Hypodermic needles are being replaced with needless connectors that use an actuator, instead of a needle. The needless connector can placed, for example, at one end of a catheter while the other end of the catheter is connected to a patient. The actuator can be inserted into an end of the needless connector.

DRAWINGS

FIGS. 8A and 83 depict a flowchart of a method for making a connector, according to one embodiment.

The drawings referred to in this description should not be understood as being drawn to scale unless specifically noted.

DESCRIPTION OF EMBODIMENTS

The description of embodiments will begin with an overview followed by a detailed description of various embodiments for providing a connector with a dual diaphragm valve.

OVERVIEW

Connectors that involve one or more moving parts can result in displacement of fluid. Displacement can be positive or negative. The phrase "positive displacement," refers to fluid being pushed out of the connector into the catheter and possibly then being pushed into the patient. The phrase "negative displacement," refers to fluid being pulled from the patient into the catheter and possibly then being pulled into the connector. Displacement can occur when an actuator is inserted into a connector or when an actuator is removed from a connector.

The terms "accessed," and "actuated," shall be used to refer to the state of the connector when an actuator is inserted into the connector. The terms "unaccessed," and "unactuated," shall be used to refer to the state of the connector when an actuator is not inserted into the connector. The term "disconnection," shall be used to refer to the act of removing the actuator from the connector.

One of the problems with negative displacement upon disconnection is if body fluids are pulled into the connector, the body fluids can coagulate potentially resulting in an obstructed connector. An obstructed connector may need to be replaced with a new connector.

Therefore, according to one embodiment, positive displacement is provided upon disconnection. Since positive displacement pushes fluids out of the connector, positive displacement prevents body fluids from being pulled into the connector, and thus, prevents obstruction due to coagulation of body fluids.

In contrast, one of the problems with positive displacement upon disconnection is that the displaced medication can be pushed into the patient potentially resulting in an overdose.

According to one embodiment, minimal positive displacement is provided. Minimal displacement prevents potential drug overdoses since a negligible amount of medication is pushed out, as will become more evident.

Figure 1A:
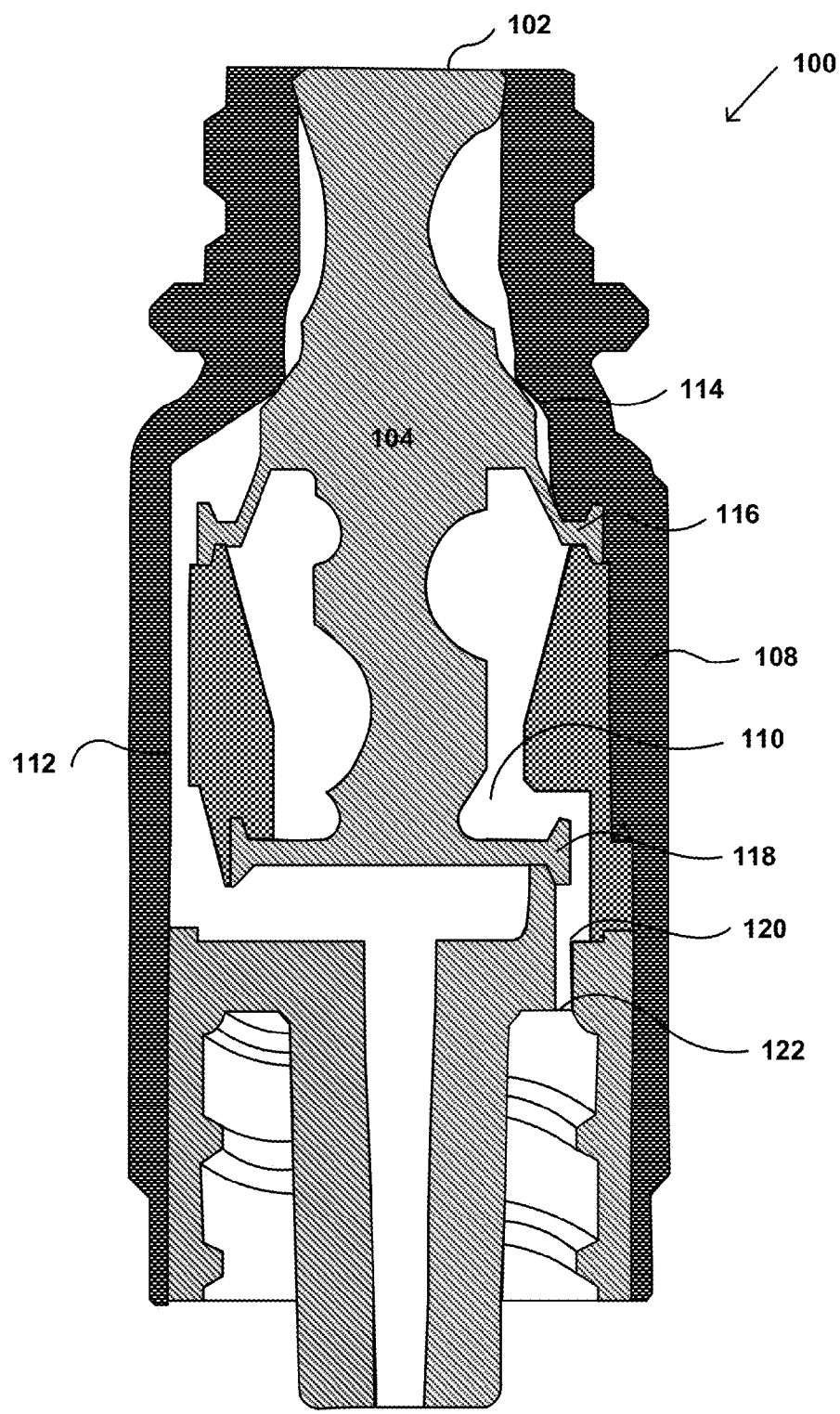
FIG. 1A depicts a side cross section of a connector that is unaccessed, according to one embodiment.
Figure 1B:
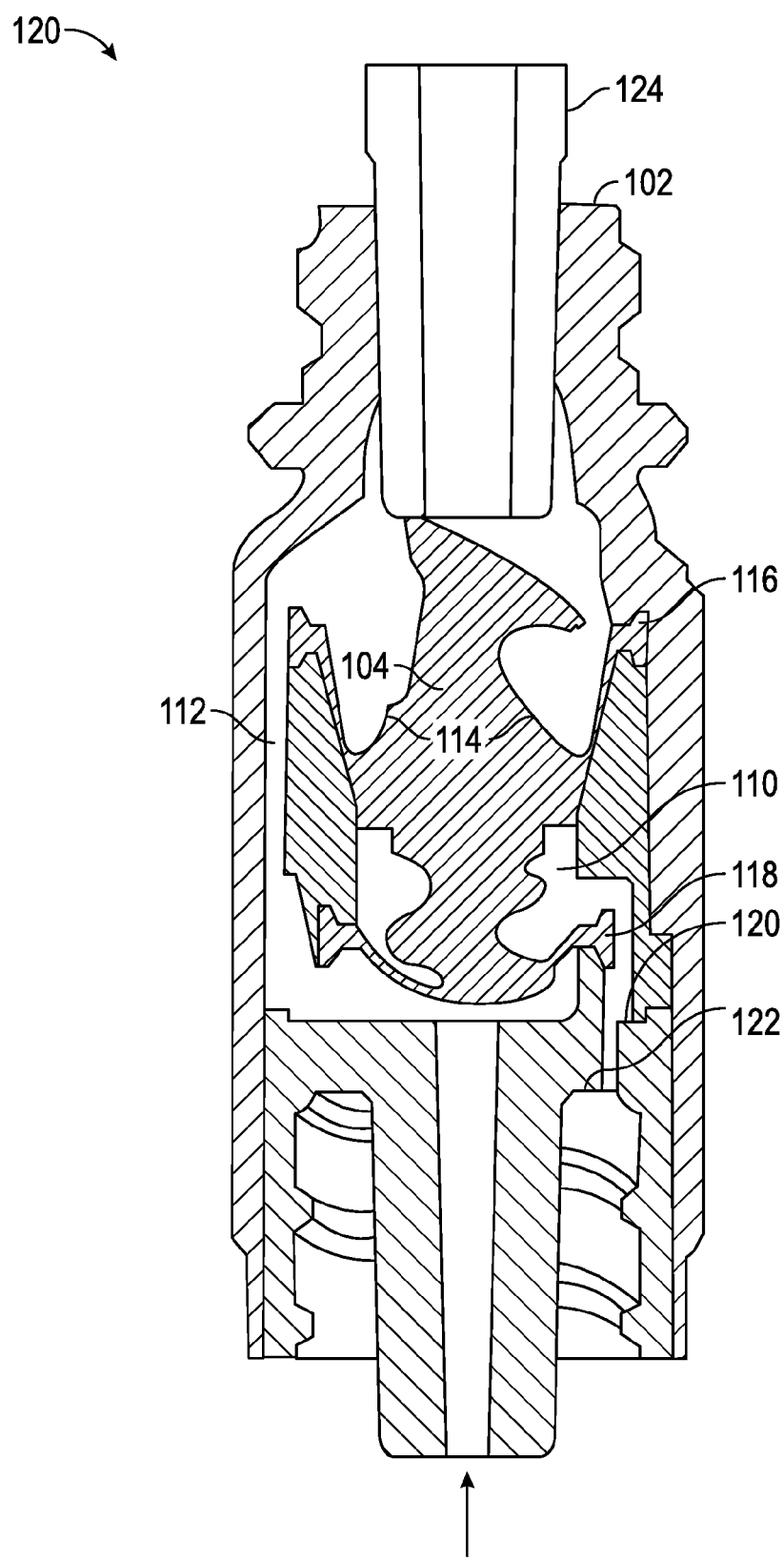
FIG. 1B depicts a side cross section of a connector that is accessed, according to one embodiment.
Figure 1C:
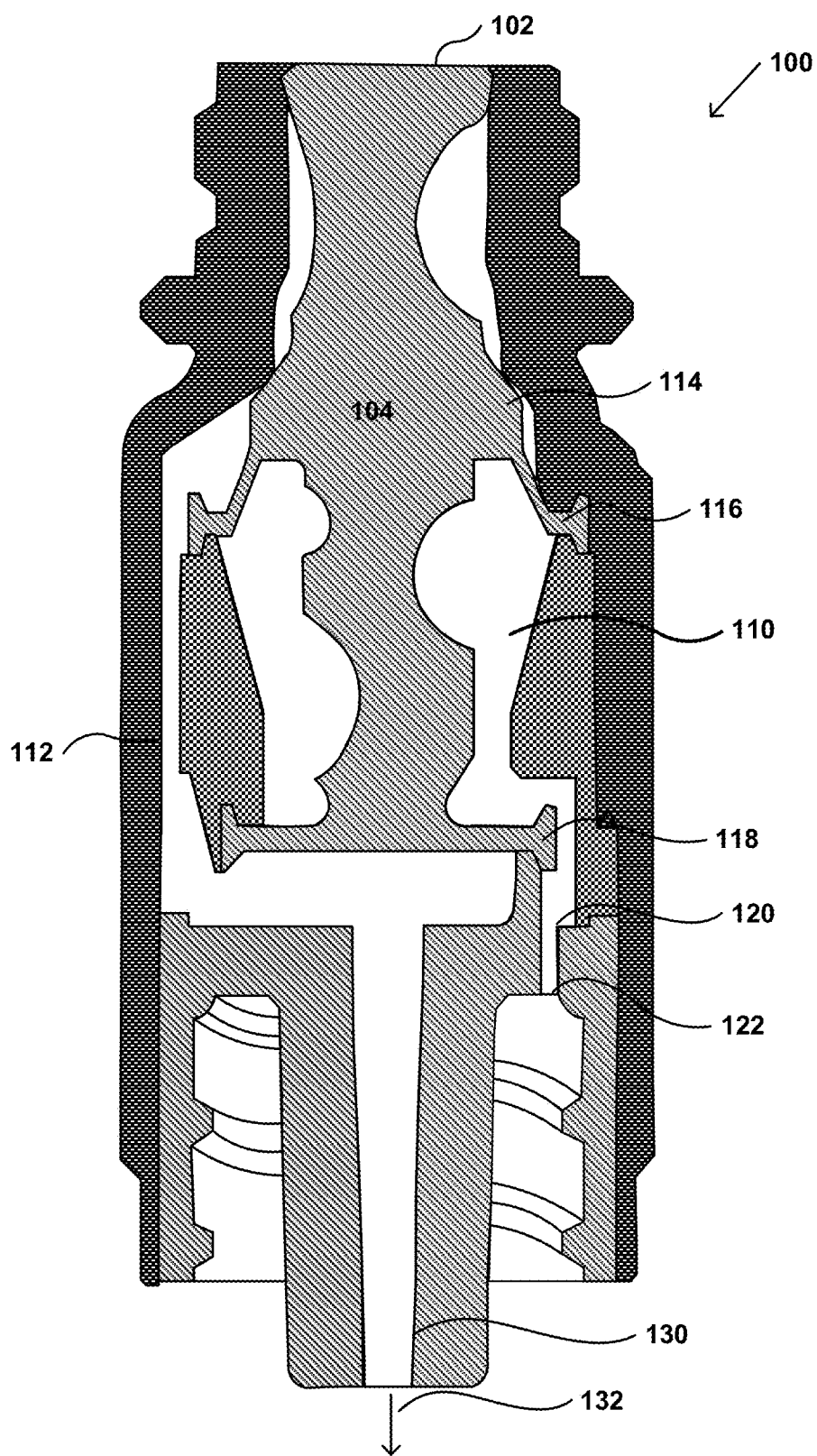
FIG. 1C depicts a side cross section of a connector upon disconnection, according to one embodiment.

FIGS. 1A-1C depict side cross section view's of a connector 100 in grey scale, according to various embodiments, where the housing is the darkest shade of grey, the valve plug and the base are in an intermediate shade of grey, and the insert is in the lightest shade of grey.

FIG. 1A depicts a side cross section view of a connector 100 that is unaccessed, according to one embodiment. The connector 100 includes a fluid flow path (FFP) 112, an air chamber 110, a housing 108, a valve plug 104 with two diaphragms 116, 118, and vent holes 120, 122, among other things. The fluid flow path 112 is depicted with lines that move from the upper right corner down to the lower left corner and the air chamber 110 is depicted with cross hatchings, according to one embodiment. The fluid flow path 112 is sealed at the top 102 of the connector 100 and at the shoulder 114 of the valve plug 104 where the valve plug 104 contacts the housing 108.

FIG. 1B depicts a side cross section view of a connector 100 that is accessed, according to one embodiment. The fluid flow path 112 is depicted with lines that move from the upper right corner down to the lower left corner and the air chamber 110 is depicted with cross hatchings, according to one embodiment. According to various embodiments, displacement is provided by the change in the volumes associated respectively with the fluid flow path 112 and the air chamber 110. For example, the inserted actuator 124 pushes the valve plug 104 downwards causing the valve plug and the associated diaphragms 116, 118 to move downwards. This is also referred to as deforming or compressing the valve plug 104 upon actuation. The volume associated with the fluid flow path 112 enlarges. Further, air is pushed out of the air chamber 110 through the vent holes 120, 122 and the volume associated with the air chamber 110 reduces in size. The seal at the top 102 and at the shoulder 114 are opened by the deformation of the valve plug 104, opening the fluid flow path 112 for fluid to flow between the actuator 124 and the bottom port 126. Negative displacement 128 occurs with fluid, such as bodily fluids, being pulled into the catheter and possibly into the connector 100. However, the medication then starts to flow from the actuator 124, through the fluid flow path 112, out the bottom port 126, through the catheter and to the patient, thus, if bodily fluids were pulled into the connector 100, they will not remain in the catheter upon actuation for the purposes of delivering fluids to the patient.

In contrast, FIG. 1C depicts a side cross section view of a connector 100 upon disconnection, according to one embodiment. The fluid flow path 112 is depicted with lines that move from the upper right corner down to the lower left corner and the air chamber 110 is depicted with cross hatchings, according to one embodiment. According to various embodiments, upon disconnection, the valve plug 104 returns to an undeformed uncompressed state when the actuator 124 is removed. The fluid flow path 112 and the air chamber 110 resume the same or approximately the same shape and volume that they had before they were accessed as depicted in FIG. 1A. The seals at the top 102 and at the shoulder 114 return. The diaphragms 116, 118 move upwards causing the fluid flow path 112's volume to reduce in size and the air chamber 110's volume to increase in size as air is pulled into the air chamber 110's volume through the vent holes 120, 122. Positive displacement 132 occurs with fluid, such as medication or bodily fluids, being pushed out the bottom port 126, into the catheter and possibly into the patient.

Therefore, according to one embodiment, it is the changes in the respective volumes of the fluid flow path and the air chamber due at least in part to the movement of the diaphragms 116, 118 that provide for positive displacement upon disconnection and negative displacement upon actuation, as discussed herein.

Components of a Connector

A connector as depicted in FIGS. 1A-1C includes various components, according to one embodiment. FIGS. 2A-2D depict components of a connector 100, according to one embodiment.

Figure 2A:
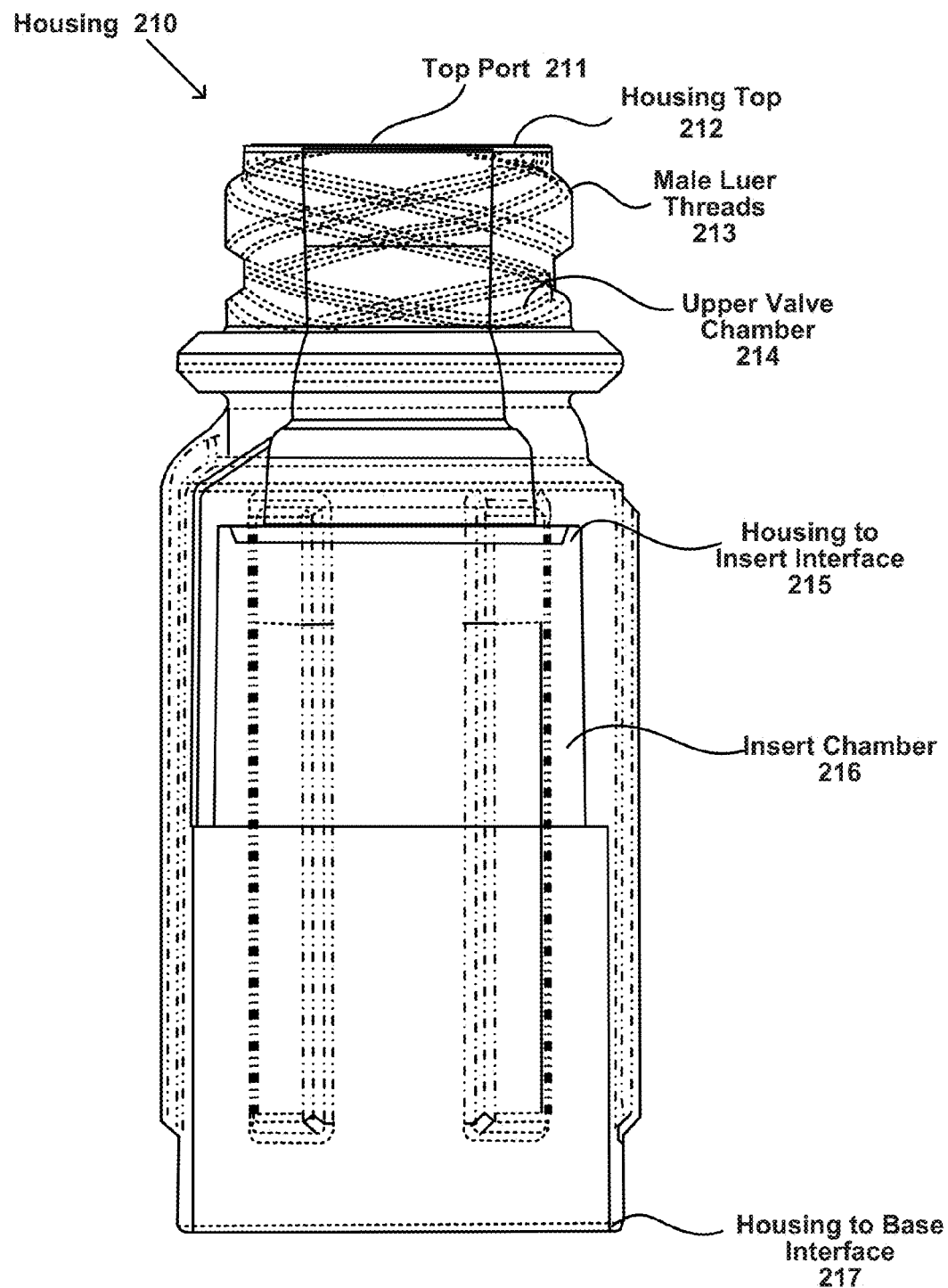
FIG. 2A depicts a housing, according to one embodiment.

FIG. 2A depicts a housing 210, according to one embodiment. For example, the housing 210 as depicted includes a top 212, a top port 211, male luer threads 213, an upper valve chamber 214, a housing to insert interface 215, an insert chamber 216, and a housing to base interface 217, according to one embodiment. The top port 211 is configured so that an actuator can be inserted into it. According to one embodiment, the top port 211 is configured so that an inserted actuator fits snugly in the top port 211. The male luer threads 213 can be used for screwing a cap associated with the actuator securely to the connector. The housing to insert interface 215 is used for connecting the housing 210 and an insert. The insert chamber 216 provides a volume for a portion of the insert to reside when the insert is placed inside of the housing 210. The housing to base interface 217 is used for connecting the housing 210 and a base. The housing 210 can include one or more ribs. The ribs are on the outside of the housing 210, according to one embodiment. According to one embodiment, at least one of the ribs is configured to provide a portion of a fluid flow path, as will become more evident.

Figure 2B:
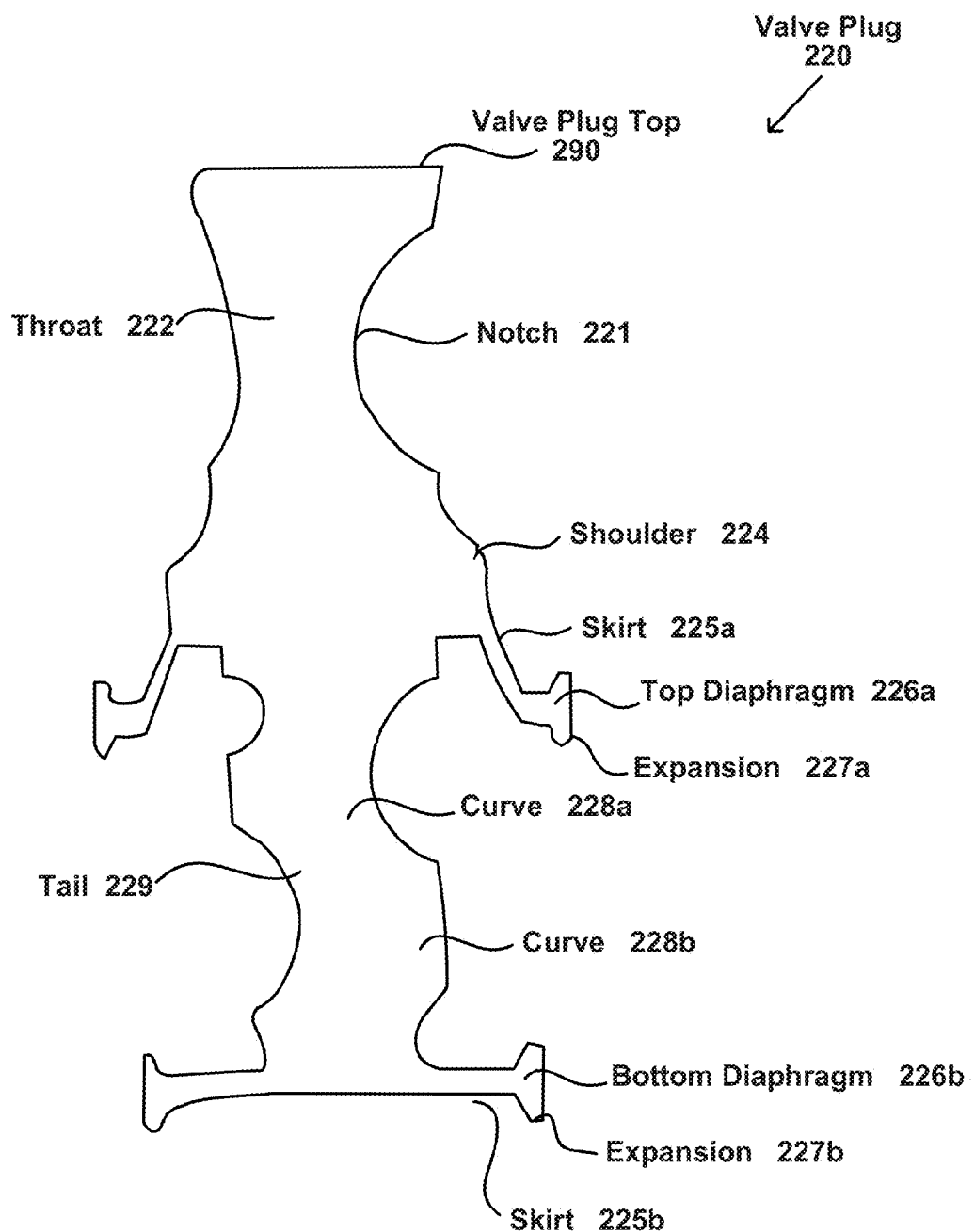
FIG. 2B depicts a side cross section of a valve plug, according to one embodiment.

FIG. 2B depicts a side cross section view of a valve plug 220, according to one embodiment. For example, the valve plug 220 as depicted includes a top 290, a throat 222, a semi-circular notch 221 on one side of the valve plug 220, a shoulder 224, a top diaphragm 226a, a bottom diaphragm 226b, skirts 225a, 225b of the respective diaphragms 226a, 226b, expansions 227a, 227b of the respective diaphragms 226a, 226b, a tail 229 between the two diaphragms 226a, 226b, and two curves 228a, 228b in the tail 229. The two diaphragms 226a, 226b are also referred to as a "dual diaphragm." According to one embodiment, the bottom diaphragm 226b has a smaller diameter than the top diaphragm 226a. The top diaphragm 226a's skirt 225a is oriented downwards. The bottom diaphragm 226b's skirt 225b is oriented horizontally. Either one or both of the skirts 225a, 225b can be oriented downwards, upwards, or horizontally, among other things, according to various embodiments. The diaphragms 226a, 226b include expansions 227a, 227b, according to one embodiment, oriented, for example, at the edges of the diaphragms 226a, 226b. The respective expansions 227a, 227b can be used, for example, as a part of holding the diaphragms 226a, 226b in place when assembled with the other connector components. As depicted, the tail 229 includes two curves 228. Although the tail 229 is depicted with two curves 228a, 228b, fewer or additional curves may be used.

According to one embodiment, the valve plug 220 is made of a single piece of material. According to one embodiment, the valve plug 220 is made of a solid piece of material. According to one embodiment, injection molded silicon can be used to make a valve plug 220 that is a single solid piece. According to one embodiment, the valve plug 220 may be a single piece of material that is hollow inside or contains an air pocket inside of it. According to one embodiment, the valve plug 220 does not require a septum or a channel that flows through it. For example, as will become more evident, a fluid flow path runs around the valve plug 220, according to one embodiment, instead of through the valve plug 220. According to another embodiment, the valve plug 220 may include more than one piece that interacts with each other.

Figure 2C:
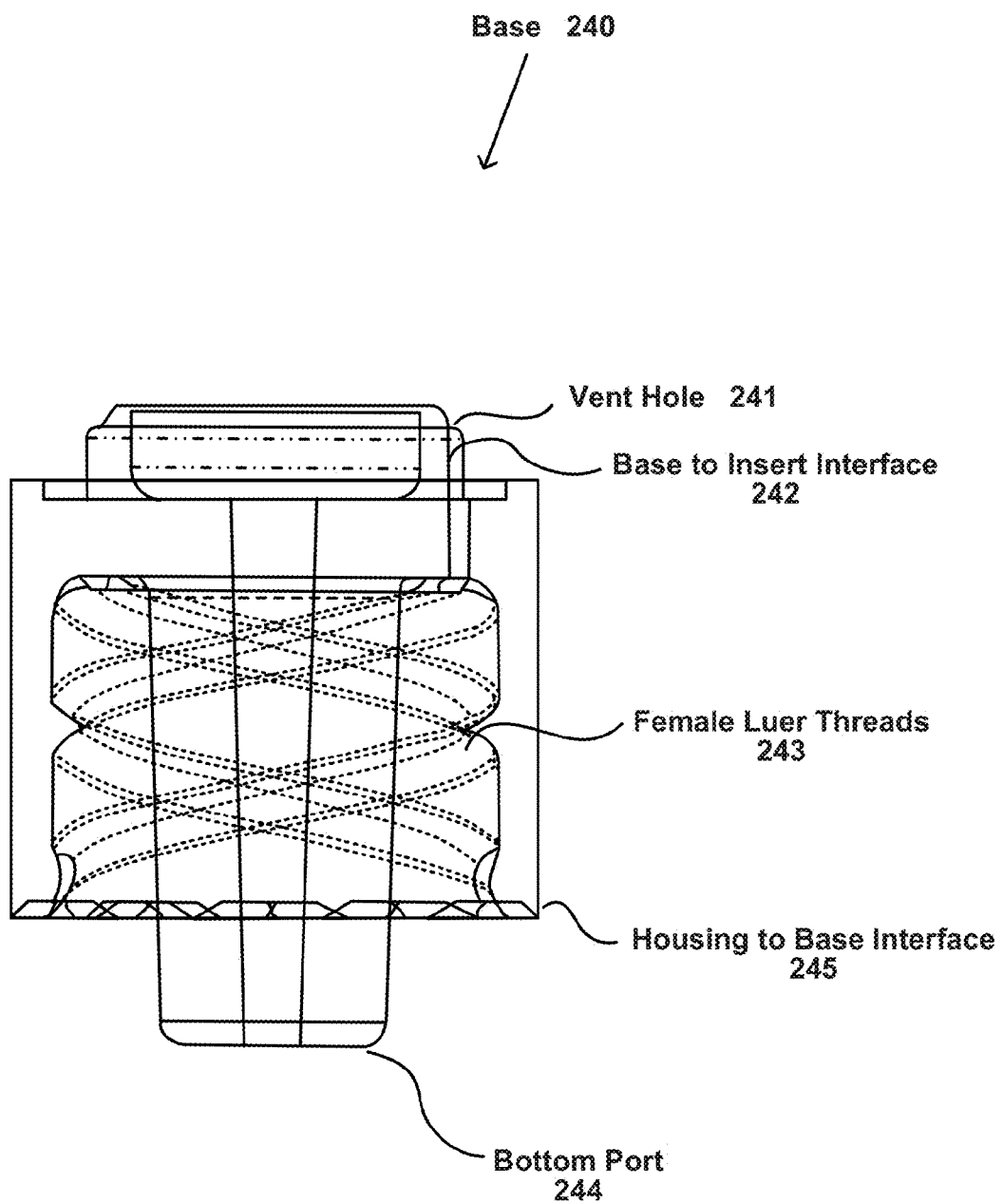
FIG. 2C depicts a base, according to one embodiment.

FIG. 2C depicts a base 240, according to one embodiment. For example, the base 240 as depicted includes a vent hole 241, an insert to base interface 242, female threads 243, a housing to base interface 245, and a bottom port 244. According to one embodiment, the vent hole 241 in the base 240 is for venting air out of an air chamber and for receiving air into the air chamber, as will become more evident. The insert to base interface 242 is for connecting an insert and the base 240. The housing to base interface is for connecting the housing 210 to the base 240. The female threads 243 can be used for connecting the connector, for example, with male threads associated with one end of a catheter. The bottom port 244 can be used for delivering fluid to a patient or for receiving fluid from a patient, for example, through a catheter.

Figure 2D:
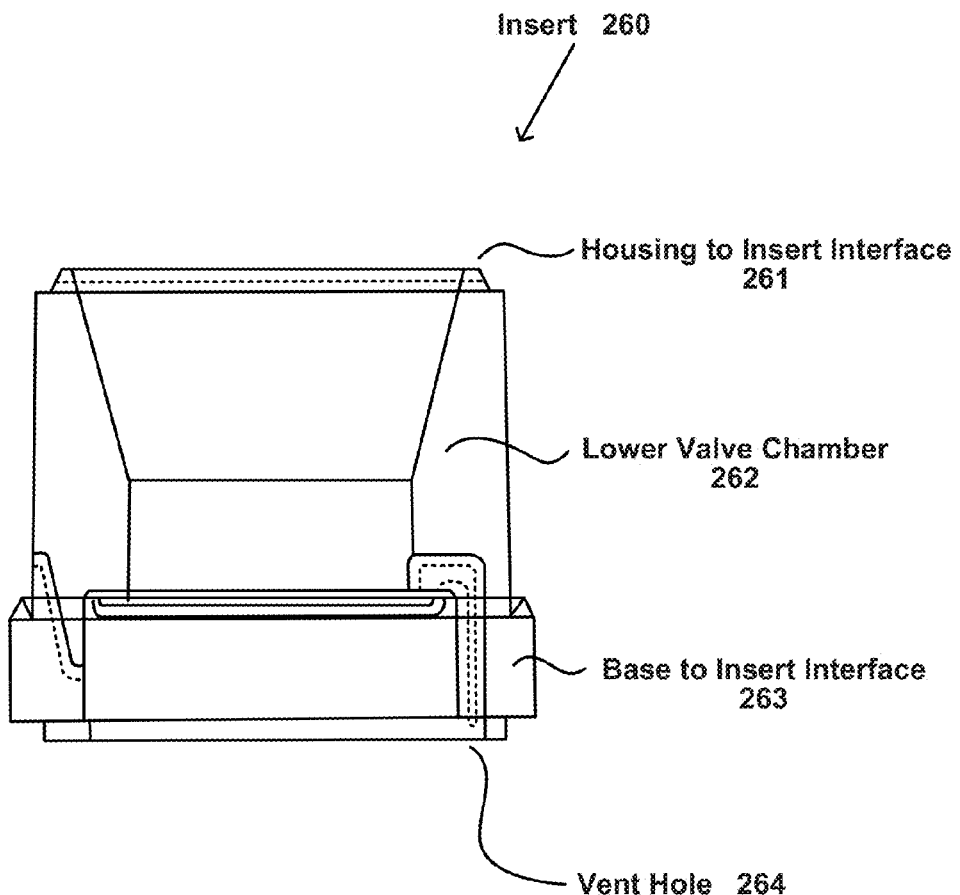
FIG. 2D depicts an insert, according to one embodiment.

FIG. 2D depicts an insert 260, according to one embodiment. For example, the insert 260 as depicted includes a housing to insert interface 261, a lower valve chamber 262, a base to insert interface 263, and a vent hole 264. The housing to insert interface 261 is for connecting the housing 210 to the insert 260. The base to insert interface 263 can be used for connecting the base 240 and the insert 260. The lower valve chamber 262, according to one embodiment, provides a volume that the lower portion of the valve plug 220 can reside when the connector is assembled. The vent hole 264 is for venting air out of the air chamber and for receiving air into the air chamber. According to one embodiment, the base 240's vent hole 241 and the insert 260's vent hole 264 are aligned with each other in order to vent air out of the air chamber and to receive air into the air chamber.

Referring to FIGS. 2A, 2C and 2D respectively, the housing 210, the base 240 and the insert 260 can be made from a substantially rigid material, such as but not limited to, polycarbonate, polyvinyl chloride (PVC), acrylonitrile butadiene styrene (ABS) or plastic. Referring to FIG. 2B, the valve plug 220 can be made of a deformable material such as, but not limited to, silicon, injection molded silicon or rubber.

As will become more evident, the housing 210, valve plug 220, base 240 and insert 260 (FIGS. 2A, 2C and 2D respectively) can be assembled to create a connector 100 (FIGS. 1A-1C). For example, the base 240 (FIG. 2C) and the insert 260 (FIG. 2D) can be connected at their respective base to insert interfaces 242, 263. The valve plug 220 can be placed in the lower valve chamber 262 of the insert 260 and the housing 210 can be placed over the valve plug 220 and a portion of the insert 260. The housing 210 and the insert 260 can be connected at their respective housing to insert interfaces 215, 261.

According to one embodiment, the various interfaces 215, 261, 217, 245, 242, 263, such as the respective housing to insert interfaces 215, 261, the housing to base interfaces 217, 245 and the base to insert interfaces 242, 263, provide for connecting respective components together. The respective components can be clamped together at the interfaces 215, 261, 217, 245, 242, 263, ultrasonically welded, or glued, among other things. An interface 215, 261, 217, 245, 242, 263 that provides for clamping, according to one embodiment, includes a "clamping area" According to one embodiment, the housing 210 and the insert 260 are press fitted together at the housing to base interfaces 217, 245. According to one embodiment, the interfaces are connected in a manner that the outer surface of the connector is smooth, and, therefore, swabable. For example, in the case of ultrasonic welding, weld points can be provided on the inside of the connector.

A Partially Assembled Connector

Figure 3:
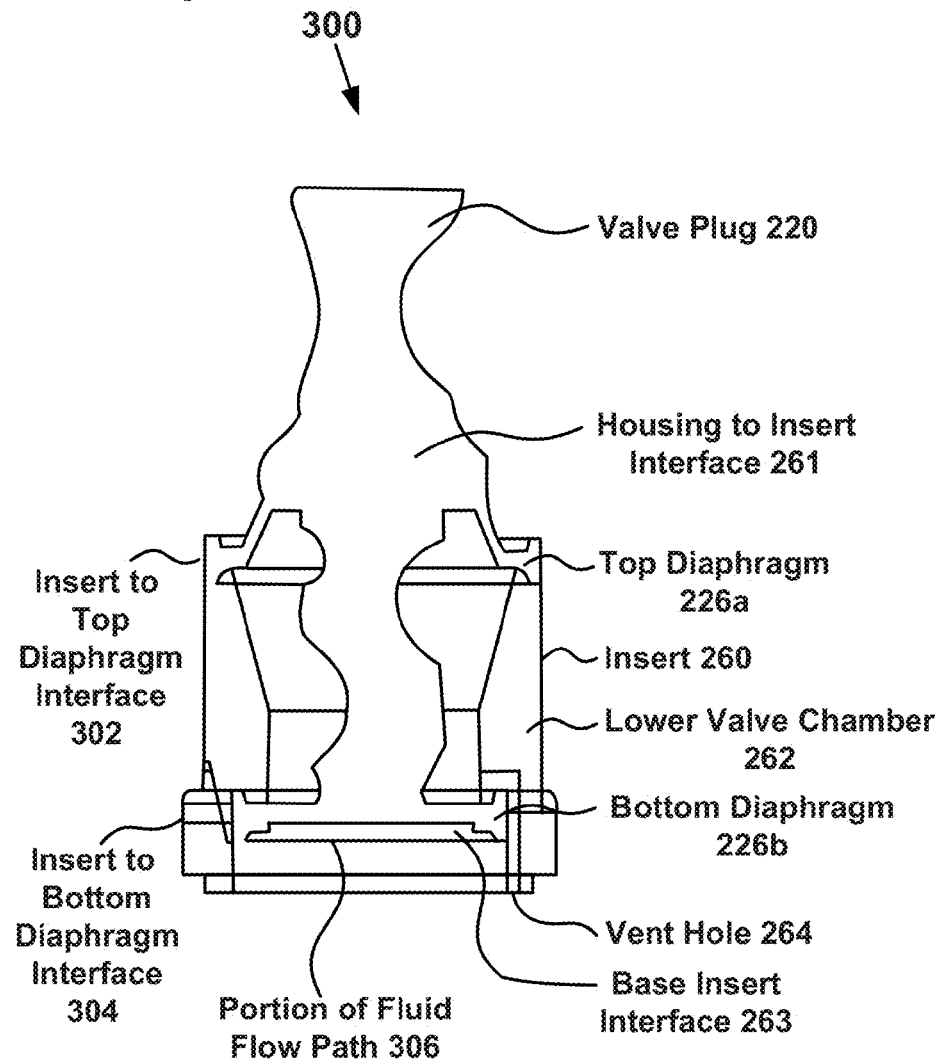
FIG. 3 depicts a side cross section of a partially assembled connector, according to one embodiment.

FIG. 3 depicts a side cross section view of a partially assembled connector 300, according to one embodiment. The partially assembled connector 300 includes a valve plug 220, an insert 260, the housing to insert interface 261, the top diaphragm 226a, the lower valve chamber 262, the bottom diaphragm 226b, the vent hole 264 in the insert 260, the base to insert interface 263, an insert to top diaphragm interface 302, an insert to bottom diaphragm interface 304, and a portion 306 of the fluid flow path 112.

As depicted in FIG. 3, the lower portion of the valve plug 220 has been inserted into the lower valve chamber 262 provided by the insert 260. The insert to top diaphragm interface 302, and the insert to bottom diaphragm interface 304 that can be used for fitting the valve plug 220 in the connector 300. According to one embodiment, the top diaphragm 226a's expansion 227a is fit snuggly between the insert 260 and the housing 210 (FIG. 2A) at the respective housing to insert interlaces 215, 261 when the housing 210 is placed over the insert 260. According to one embodiment, the insert 260 and the housing 210 (FIG. 2A) provides respective notches that conform respectively to the top and bottom diaphragm's 226a, 226b expansions 227a, 227b. According to one embodiment, the notches provide a tight fit for the expansions 227a, 227b.

Top Cross Section View

Figure 4:
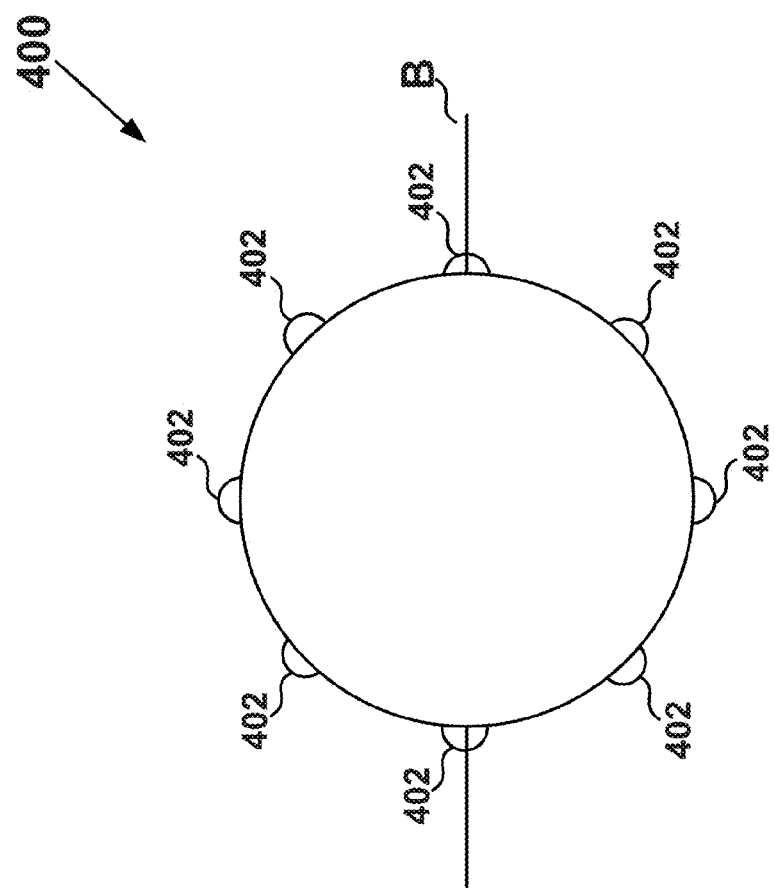
FIG. 4 depicts a top cross section view of the outline of an assembled connector, according to one embodiment.
Figure 5:
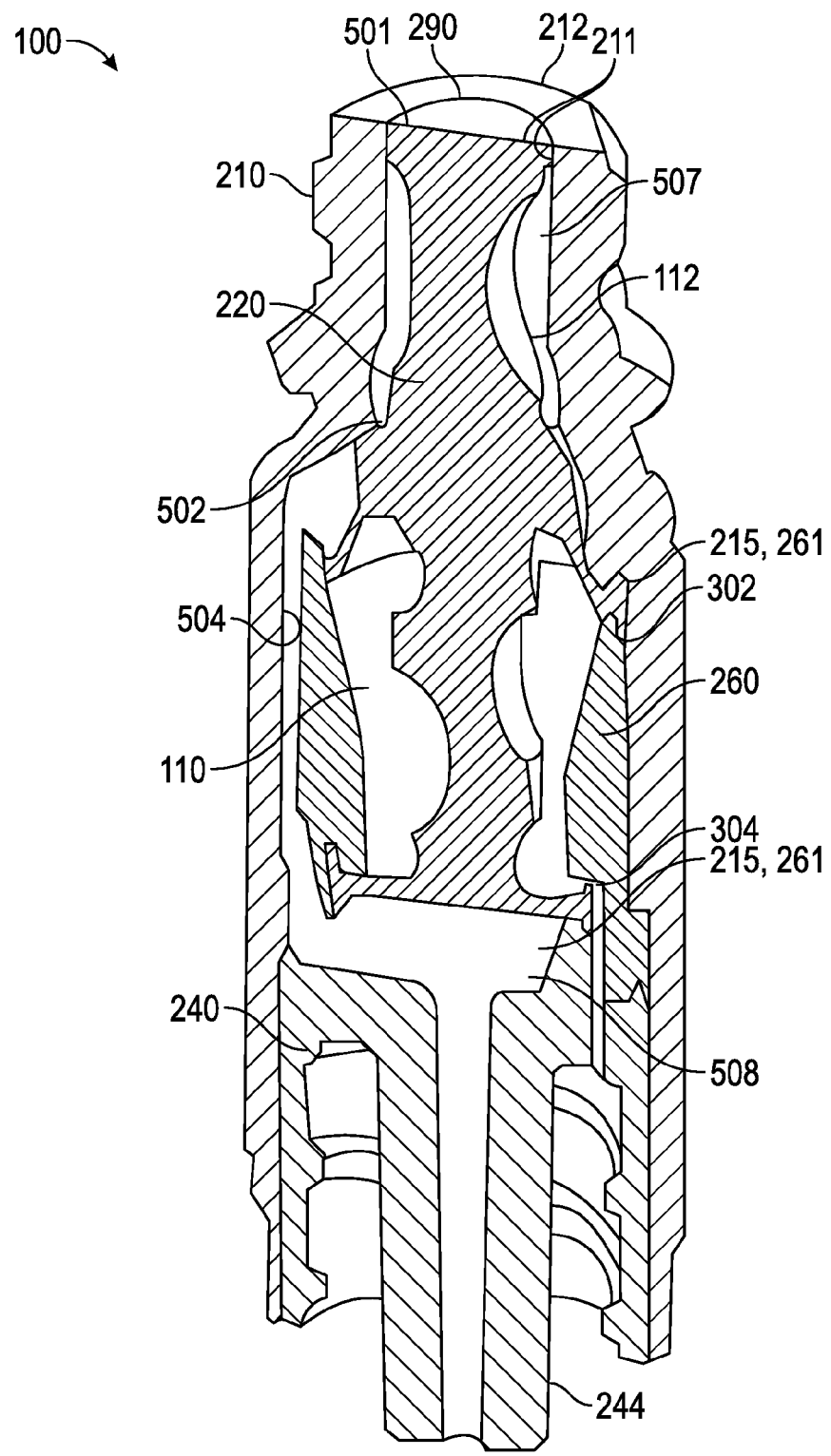
FIG. 5 depicts a side cross section view of an empty assembled connector from cross section, which runs at least through one rib, according to one embodiment.
Figure 6:
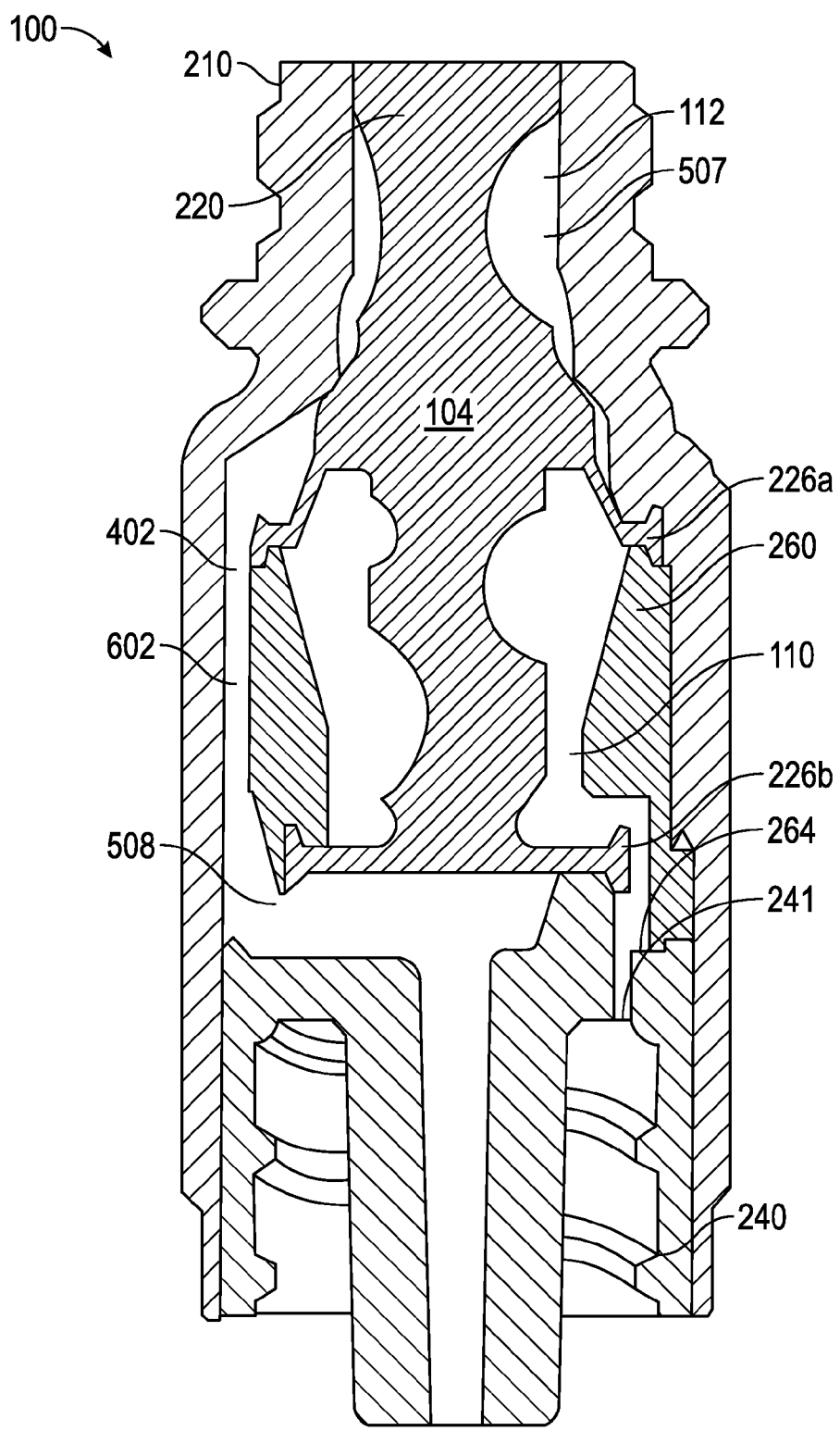
FIG. 6 depicts a side cross section view of an assembled connector containing fluid from cross section, which runs through at least one rib, according to one embodiment.

FIG. 4 depicts a top cross section view 400 of the outline of an assembled connector, according to one embodiment. FIG. 4 also depicts ribs 402 and cross section line B of the connector that will be used for depicting side cross section views of the assembled connector. Cross section line B runs through at least one rib 402. FIG. 5 depicts a side cross section view of an empty assembled connector from cross section line B, according to one embodiment. FIG. 6 depicts a side cross section view of an assembled connector that contains fluid from cross section line B, according to one embodiment. According to one embodiment, a portion of the fluid flow path runs through one or more ribs 402.

Unactuated Connector

Figure 7:
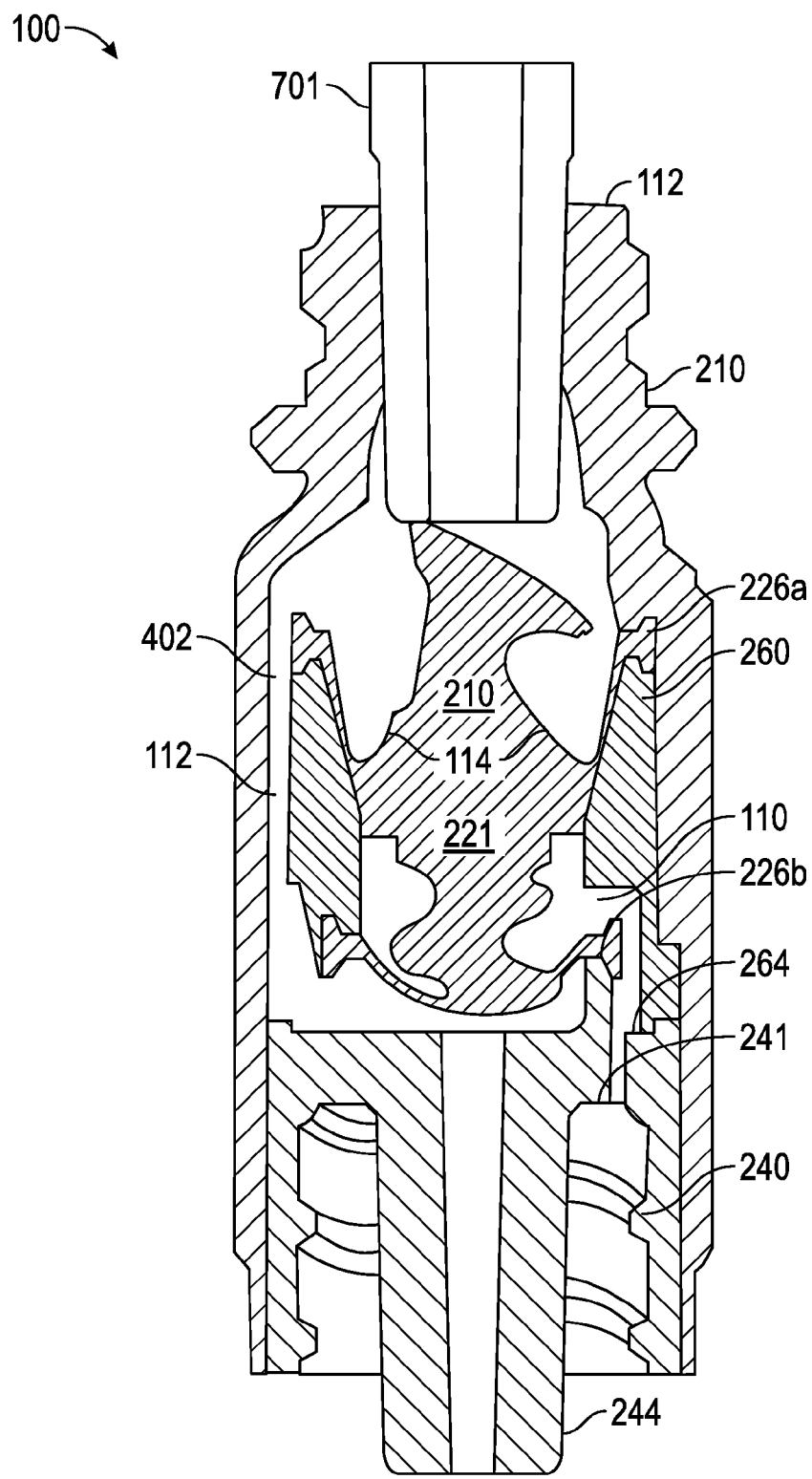
FIG. 7 depicts a side cross section view of an actuated connector, according to one embodiment.

FIGS. 5-7 depict side cross section views of a connector 100 in grey scale, according to various embodiments, where the housing 210 is the darkest shade of grey, the valve plug 220 and the base 240 are in an intermediate shade of grey, and the insert 260 is in the lightest shade of grey.

FIG. 5 depicts a side cross section view of an empty unactuated connector through the cross section line B, which runs through at least one rib, according to one embodiment. The depicted connector 100 includes a housing 210, a valve plug 220, an insert 260 and a base 240. The depicted connector 100 also includes a housing top 212, top port 211, valve plug top 290, fluid flow path 112, portion 507 of the fluid flow path 112, housing to insert interfaces 215, 261, insert to top diaphragm interface 302, insert to bottom diaphragm interface 304, base to insert interfaces 242, 263, portion 508 of fluid flow path 112, bottom port 244, a top seal 501, a shoulder seal 502, the housing inner wall 504 and an air chamber 110.

The assembled connector 100 provides seals 501, 502, according to one embodiment. For example, the assembled connector 100 provides a top seal 501 where the valve plug top 290 interfaces with the housing top 212. According to one embodiment, the interface between the valve plug top 290 and the housing top 212 is a smooth surface that is swabable. In another example, the assembled connector 100 provides a shoulder seal 502 where the valve plug 220's shoulder 224 interfaces with an inner wall 504 of the housing 210.

The top diaphragm 226a's expansion 227a is sandwiched between the insert 260 and the housing 210 at the housing to insert interfaces 215, 261, according to one embodiment. The bottom diaphragm 226b's expansion 227b is fit snuggly, according to one embodiment, at the insert to bottom diaphragm interfaces 304. For example, the expansion 227b can be fit into notches associated with the insert 260 at the insert to bottom diaphragm interfaces 304.

FIG. 5 also depicts portions 507, 508 of the fluid flow path 112 and the air chamber 110 that are separated at least in part by the valve plug 220. The air chamber 110 is provided by, among other things, the lower surface of the top diaphragm 226a, the upper surface of the bottom diaphragm 226b, and the inner walls of the insert 260, according to one embodiment.

The valve plug 220, according to one embodiment, can be deformed or compressed when an actuator is inserted into the top port 211. As depicted in FIG. 5, the valve plug 220 is not deformed and not compressed because an actuator is not inserted.

FIG. 6 depicts a side cross section view of an unactuated connector that contains fluid through cross section line B, which runs through at least one rib, according to one embodiment. According to one embodiment, one of the ribs 402 provides a portion 602 of the fluid flow path 112, according to one embodiment. As shown, FIG. 6 depicts a connector 100 that includes a portion 507 of the fluid flow path 112, a rib 402, diaphragms 226a, 226b, insert 260, air chamber 110, vent holes 264, 241, base 240, housing 210, valve plug 220, fluid flow path 112, portion 602 of the fluid flow path 112, and portion 508 of fluid flow path 112.

FIG. 6 further depicts how the two diaphragms 226a, 226b can be used to separate the fluid flow path 112 from the air chamber 110, according to one embodiment. For example, the air chamber 110 is formed, at least in part, by the inner walls of the insert 260, the lower surface of the top diaphragm 226a, the outer surfaces of the valve plug's tail 229, and the upper surface of the bottom diaphragm 226b. The fluid flow path 112 is formed, at least in part, by portions of the housing 210, the insert 260, the base 240, and the valve plug 220. More specifically, as depicted, the fluid flow path 112 is formed, at least in part, by the inner walls of the upper portion of the housing 210 around the throat 222 of the valve plug 220, the inner walls of the housing 210 around the valve plug 220's shoulder 224 and the upper surface of the top diaphragm 226a, one of the housing 210s ribs 402, a lower region of the insert 260 near the bottom diaphragm 226b, the lower surface of the bottom diaphragm 226b, and the bottom port 244 of the base 240. The fluid flow path 112 is separated from the air chamber 110, at least in part, by the upper surface of the top diaphragm 226a and the lower surface of the bottom diaphragm 226b.

Actuated Connector

FIG. 7 depicts a side cross section view of an actuated connector 100, according to one embodiment. FIG. 7 further depicts an actuator 701, a housing 210, a valve plug 220, the base 240, the fluid flow path 112, the insert 260, the air chamber 110, a rib 402, the top port 211, the diaphragms 226a, 226b, the vent holes 264, 241, and bottom port 244.

As depicted in FIG. 7, an actuator 701 is inserted into the connector 100 the connector 100 through the top port 211 for delivering fluid or receiving fluid, according to one embodiment. For example, when the valve plug 220 is deformed upon actuation, the fluid flow path 112 opens between the top port 211 and the bottom port 244, as depicted in FIG. 7.

More specifically, as depicted, the valve plug 220's tail 229 compresses (also known as "deforms"), the two diaphragms 226a, 226b stretch downward, and the valve plug top 290 and shoulder 224 move downward. When the valve's top 290 and shoulder 224 move downward, the seals 501, 502 depicted in the unactuated connector on FIGS. 5 and 6 are opened up providing a fluid flow path 112 that is open between the top port 211 and the bottom port 244 as depicted in FIG. 7. A fluid flow path 112 that is open between the top port 211 and the bottom port 244 shall also be referred to herein as "an open fluid flow path." The air chamber 110 and the fluid flow path 112 are still separated at least in part by the dual diaphragm 226a, 226b upon actuation, according to one embodiment.

According to one embodiment, the fluid flow path 112 is not required to go through the valve plug 220 but instead can go around the valve plug 220 as depicted in FIG. 7. For example, upon actuation, the single fluid flow path 112 enables fluid that flows from the tip of the actuator 701 to interact, at least in part, with the valve plug top 290, the valve plug 220's shoulder 224, the upper surface of the top diaphragm 226a, the inner walls of one of the ribs 402, the underneath surface of the bottom diaphragm 226b and the inner walls of the bottom port 244, according to one embodiment. Similarly, if fluid were being drawn from a patient, the fluid would flow in the opposite direction, according to one embodiment.

According to one embodiment, an assembled connector 100 as depicted in FIGS. 1A-1D and FIGS. 5-7 is approximately 1.25 inches long and approximately 0.4 inches in diameter. According to one embodiment, the length of an assembled connector 100 can range from approximately 1 inch to 2 inches and the diameter of an assembled connector 100 can range from approximately 0.4 inch to 1 inch. The width of the walls associated with the connector's components, such as the housing 210, the base 240, and the insert 260, among others, can vary, according to one embodiment. For example, the walls of the components can be made thicker or narrower. According to one embodiment, the thickness of the walls of the components can be varied as a part of providing minimal displacement.

Minimal Displacement

As discussed herein, displacement of fluid typically occurs when a connector includes moving parts, such as a valve plug. With positive displacement, an overdose can occur due medication being pushed into the patient. However, according to various embodiments, minimal positive displacement is provided at least in part by the dual diaphragm. For example, the volumes associated with the connector, such as the fluid flow path and the air chamber, are small, according to one embodiment. Further, the dual diaphragm takes up space inside of the connector resulting in less space for fluids and air, according to one embodiment.

Further, the movements of the two diaphragms' counteract each other, according to one embodiment. For example, referring to FIG. 1B, upon actuation, both of the diaphragms 116, 118 move downwards. The movement of the top diaphragm 116 enlarges the fluid flow path's 112 volume while the movement of the bottom diaphragm 118 downwards decreases the fluid flow path's 112 volume. The top diaphragm's 116 movement downward increases the fluid flow path's 112 volume while the bottom diaphragm's 118 movement downward decreases the fluid flow path's 112 volume, which reduces the net volume change in comparison to a connector that does not provide the counter balancing between two diaphragms 116, 118 on a fluid flow path 112's volume. Further, the top diaphragm 116 moves downwards more than the bottom diaphragm 118 does which results in the fluid flow path's 112 volume enlarging and the air chamber's 110 volume decreasing.

By using two diaphragms 116, 118 where one increases the fluid flow path's 112 volume and the other decreases the fluid flow path's 112 volume, according to one embodiment, a smaller net volume change in comparison to a connector that does not use a diaphragm or that uses only one diaphragm. For example, a valve plug 104 that included two diaphragms 116, 118 could replace more space than a valve plug that included no diaphragm or only one diaphragm. Thus, minimal negative displacement is provided upon actuation, at least in part, by the space that the valve plug 104 occupies and the counter balancing movements of the two diaphragms 116, 118, according to one embodiment.

As can be seen, according to one embodiment, minimal positive displacement can also be provided due to the relative sizes between the valve plug 104, the volumes associated with the fluid flow path 112 and the air chamber 110, and the counter balancing of the two diaphragms 116, 118, among other things. More specifically, referring to FIG. 1C, when the actuator is removed from the connector 100, both diaphragms 116, 118 move upwards. The movement of the top diaphragm 116 upwards reduces the fluid flow path's 112 volume while the movement of the bottom diaphragm 118 upwards increases the fluid flow path's 112 volume. The top diaphragm's 116 movement upwards, which decreases the fluid flow path's 112 volume, while the bottom diaphragm's 118 movement upwards, which increases the fluid flow path's 112 volume, reduces the net volume change in comparison to a connector that does not provide counter balancing of two diaphragms on a fluid flow path's volume.

Therefore, according to various embodiments, the counter balancing effects of the movements of the two diaphragms 116, 118 on the fluid flow path's 112 volume provides, at least in part, for minimal displacement.

Further, referring to FIGS. 1A-1C, it is the changes in the respective volumes of the fluid flow path 112 and the air chamber 110 due at least in part to the movement of the diaphragms 116, 118 that provide for positive displacement 132 upon disconnection and negative displacement 128 upon actuation, according to one embodiment.

For example, referring to FIG. 1B, upon actuation, the top diaphragm 116 moves downwards more than the bottom diaphragm 118 does which results in the fluid flow path's 112 volume increasing and the air chamber's 110 volume decreasing. Increasing the fluid flow path's 112 volume while decreasing the air chamber's 110 volume provides for negative displacement 128, according to one embodiment. Thus, minimal negative displacement is provided upon actuation, at least in part, by the space that the valve plug 104 occupies or the counter balancing movements of the two diaphragms 116, 118, or a combination thereof, according to one embodiment.

Further, referring to FIG. 1C, upon disconnection, the top diaphragm 116 moves upwards more than the bottom diaphragm 118 does which results in the fluid flow path's 112 volume decreasing and the air chamber's 110 volume increasing. Decreasing the fluid flow path's 112 volume while increasing the air chamber's 110 volume provides for positive displacement, according to one embodiment. Thus, minimal positive displacement is provided upon disconnection, at least in part, by the space that the valve plug 104 occupies and the counter balancing movements of the two diaphragms 116, 118, according to one embodiment.

Back Pressure

Back pressure on a connector occurs when a patient coughs, regurgitates, or their blood pressure spikes, among other things. Referring to FIG. 5, back pressure applies pressure on the underneath surface of the bottom diaphragm 226b. Fluid interacts with the top surface of the top diaphragm 226a and the underneath surface of the bottom diaphragm 226b. Since the surface area of the bottom diaphragm 226b that is interacting with fluid is larger than the surface area of the top diaphragm 226a that is interacting with fluid, according to one embodiment, there will be more force upwards than downwards, which will cause the valve plug 220 to push upwards. For example, when the valve plug 220 is pushed upwards due to back pressure and the larger surface area of the bottom diaphragm 226b interacting with fluid, the seals 501, 502 at the shoulder and at the top of the valve plug 220 become stronger. Therefore, according to one embodiment, a slit in a valve plug that enables the valve plug to expand is not required to prevent fluids from leaking during back pressure.

Method of Creating a Connector

Figure 8A:
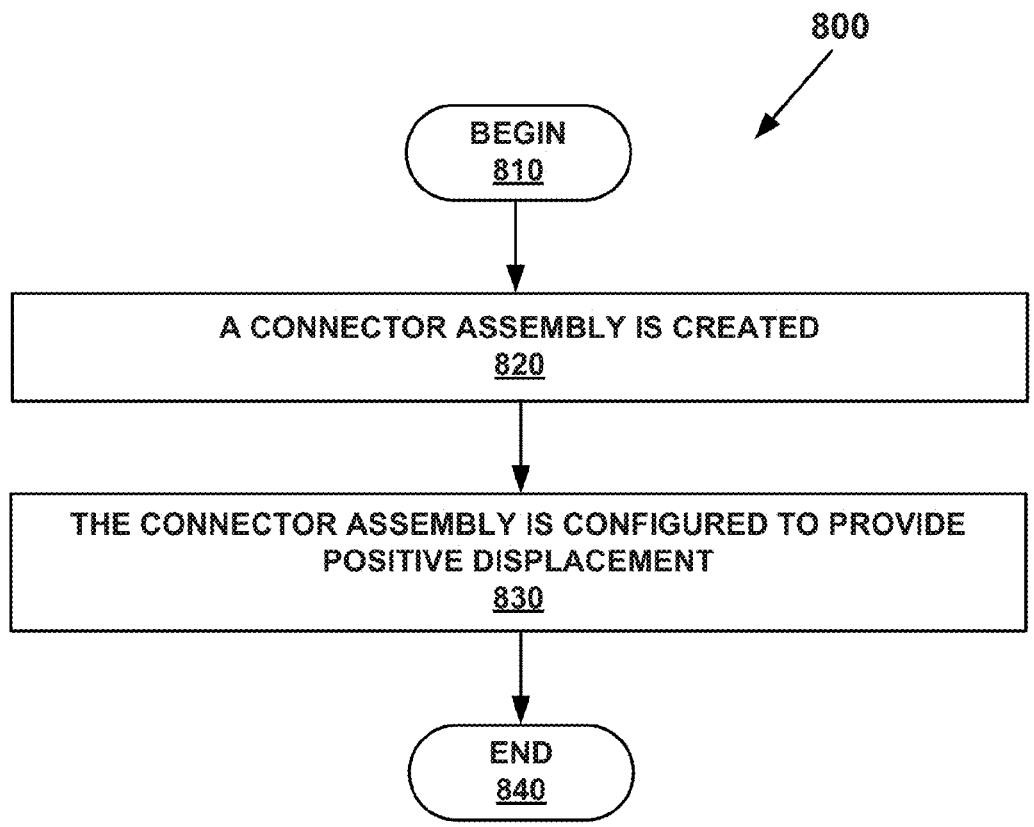

FIGS. 8A and 83 depict a flowchart for a method of creating a connector, according to one embodiment. The description of flowchart 800 shall refer to FIGS. 5, 6 and 7.

At 810, the method begins.

At 820, referring to FIGS. 5 and 6, a connector assembly is created.

For example, at 822, an insert 260 is securely connected with a base 240, for example, at the base to insert interfaces 242, 263. Various methods can be used for securely connecting the insert 260 to the base 240, such as, ultrasonic welding, clamping, gluing, screwing components together, among other things. The base 240 includes a bottom port 244. An air chamber 110 is provided, at least in part, by the insert 260.

At 824, a valve plug 220 is inserted into the insert 260. The valve plug 220 includes two diaphragms 226a, 226b.

At 826, a housing 210 is placed over the valve plug 220 and the insert 260. The housing 210 includes a top port 211. A single fluid flow path 112 flows between the bottom port 244 and the top port 211, and the two diaphragms 226a, 226b separate the air chamber 110 and the single fluid flow path 112.

At 828, the housing 210 is securely connected with the base 240, for example, at the housing to base interface 217, 245. Various methods can be used for securely connecting the housing 210 and the base 240, such as, ultrasonic welding, clamping, gluing, screwing components together, among other things.

At 830, referring to FIG. 1C, the connector assembly is configured to provide positive displacement 132 due to a volume associated with the single fluid flow path 112 decreasing and a volume associated with the air chamber 110 increasing when the valve plug 220 returns to an undeformed state by removing an actuator from the top port 211.

For example, as discussed herein, the two diaphragms 116, 118 counteracting each other upon disconnection providing for positive displacement 132. More specifically, according to one embodiment, the air chamber 110 is formed, at least in part, by the inner walls of the insert 260, the lower surface of the top diaphragm 226a, the outer surfaces of the valve plug's tail 229, and the upper surface of the bottom diaphragm 226b. Further, the fluid flow path 112 is formed, at least in part, by the inner walls of the upper portion of the housing 210 around the throat 222 of the valve plug 220, the inner walls of the housing 210 around the valve plug 220's shoulder 224 and the upper surface of the top diaphragm 226a, one of the housing 210's ribs 402, a lower region of the insert 260 near the bottom diaphragm 226b, the lower surface of the bottom diaphragm 226b, and the bottom port 244 of the base 240, according to one embodiment.

The top diaphragm 226a moves upwards more than the bottom diaphragm 226b does which results in the fluid flow paths 112 volume decreasing and the air chamber's 110 volume increasing, according to one embodiment. Decreasing the fluid flow path's 112 volume while increasing the air chamber's 110 volume provides for positive displacement, according to one embodiment. Therefore, according to one embodiment, it is the changes in the respective volumes of the fluid flow path 112 and the air chamber 110 due, at least in part, to the movement of the diaphragms 226a, 226b that provide for positive displacement upon disconnection.

At 840, the process ends.

Figure 9:
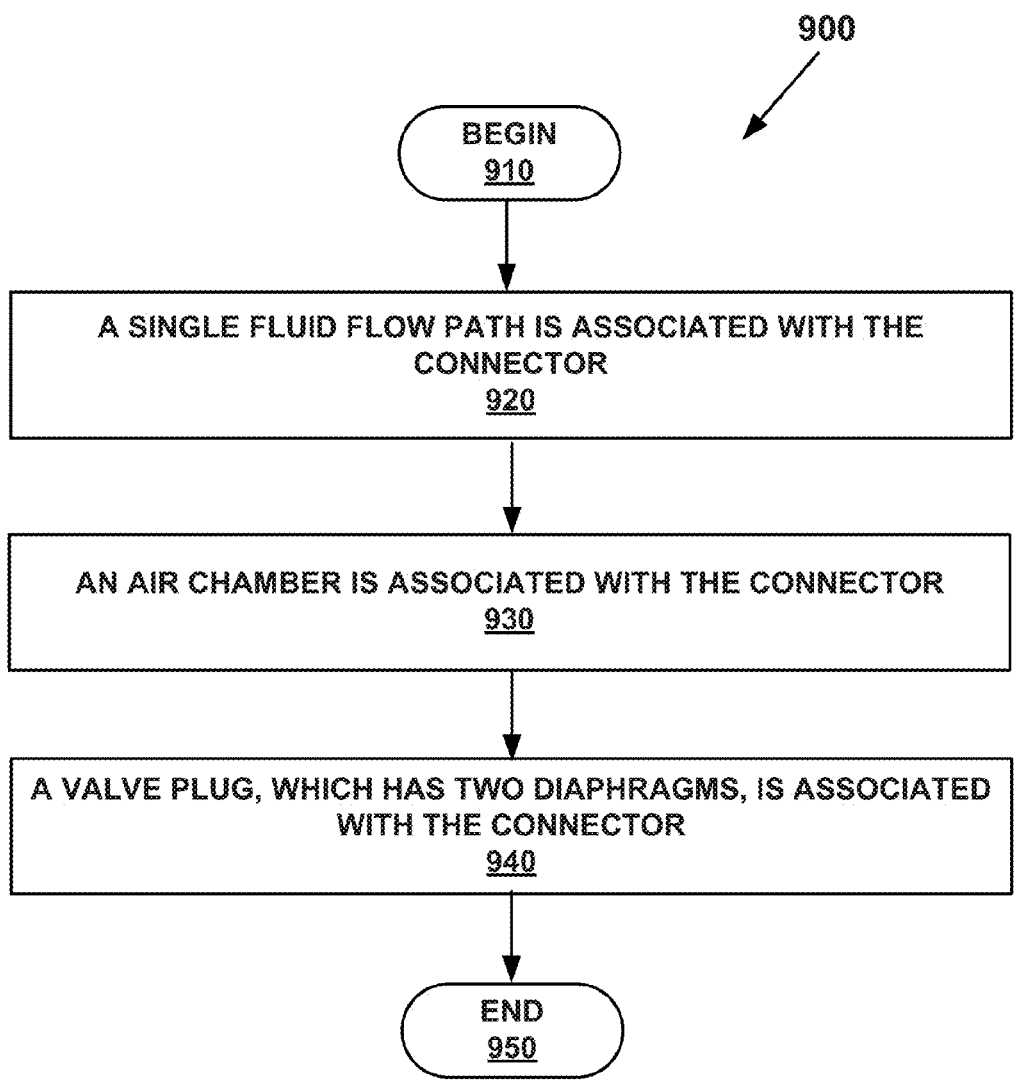
FIG. 9 is a flow chart for a method of making a connector, according to another embodiment.

FIG. 9 is a flow chart for a method of making a connector, according to another embodiment.

At 910, the method begins.

At 920, a single fluid flow path 112 is associated with the connector 100. The single fluid flow path 112 is configured for delivering fluid to a person and configured for receiving fluid from a person. For example, referring to FIGS. 2B and 5, the fluid flow path 112 is formed, at least in part, by inner walls of an upper portion of the housing 210 around a throat 222 of the valve plug 220, inner walls of the housing 210 around a shoulder 224 of the valve plug 220, the upper surface of a first 226a of the two diaphragms, a rib 402 of the housing 210, a lower region of the insert 260 near a second 226b of the two diaphragms, the lower surface of the second diaphragm 226b, and a bottom port 244 of the base 240, according to one embodiment.

At 930, an air chamber 110 is associated with the connector 100. Referring to FIG. 13, the air chamber 110 is configured for expelling air from the air chamber 110 when an actuator 124 is inserted into the connector 100 and, referring to FIG. 1C, for receiving air into the air chamber 110 when the actuator 124 is removed from the connector 100. For example, referring to FIGS. 2B and 5, the air chamber 110 is formed, at least in part, by the inner walls of the insert 260, the lower surface of a first 226a of the two diaphragms, the outer surface of a tail 229 of the valve plug 220, and the upper surface of a second 226b of the two diaphragms, according to one embodiment.

At 940, a valve plug 104 that includes two diaphragms 116, 118 is associated with the connector 100. Referring to FIG. 1C, the connector 100 provides positive displacement 132, at least in part, due to a volume associated with the single fluid flow path 112 decreasing and a volume associated with the air chamber 110 increasing, returning the valve plug 104 and the two diaphragms 116, 118 to an undeformed and uncompressed state upon removal of an actuator from the connector 100.

At 950, the method ends.

According to another embodiment, the connector is configured to provide negative displacement due to a volume associated with the air chamber 110 decreasing and a volume associated with the single fluid flow path 112 increasing, as discussed herein.

Further, as discussed herein, minimal positive displacement can be provided, at least in part, by the movements of the two diaphragms 116, 118 counteract each other or the space that the valve plug 104 occupies, or a combination thereof, according to various embodiments.

According to one embodiment, the methods 800, 900 of making a connector 100, as depicted in FIGS. 8A, 8B and 9, provide a connector 100 as depicted in FIGS. 1A-7. For example, referring to FIGS. 1A-1C, either of the methods 800, 900 (FIGS. 8A, 8B, and 9) for making a connector 100 provide a connector 100 comprising a single fluid flow path 112, an air chamber 110 and a valve plug 104 where the single fluid flow path 112 is configured for delivering fluid to a person and configured for receiving fluid from a person, the air chamber 110 is configured for expelling air from the air chamber 110 when an actuator 124 is inserted into the connector 100 and for receiving air into the chamber 110 when the actuator 124 is removed from the connector 100, and the valve plug 104 comprising two diaphragms 116, 118 that separate the air chamber 110 from the single fluid flow path 112, wherein valve plug 104 is configured for creating positive displacement 132 (FIG. 1C) by returning the valve plug 104 to its uncompressed state when the actuator 124 is removed from the connector 100.

In a second example, referring to FIGS. 5 and 6, either of the methods 800, 900 (FIGS. 8A, 8B, and 9) for making a connector 100 provide a connector 100 that includes a housing 210, a base, 240, insert 260 and a valve plug 220. The housing 210 includes a top port 211. The base 240 includes a bottom port 244. The housing 210 is securely connected to the base 240. The insert 260 is securely connected to the base 240. The insert 260 is inside a portion of the housing 210. The single fluid flow path 112 is inside a portion of the housing 210. The valve plug 220 includes two diaphragms 226a, 226b. The valve plug 220 is inside a volume formed by portions of the insert 260 and the housing 210. The connector 100 is configured to provide positive displacement when the valve plug 220 returns to an undeformed state upon removal of an actuator from the top port 211.

CONCLUSION

Example embodiments of the subject matter are thus described. Although the subject matter has been described in a language specific to structural features and/or methodological acts, it is to be understood that the subject matter defined in the appended claims is not necessarily limited to the specific features or acts described above. Rather, the specific features and acts described above are disclosed as example forms of implementing the claims.

Various embodiments have been described in various combinations and illustrations. However, any two or more embodiments or features may be combined. Further, any embodiment or feature may be used separately from any other embodiment or feature. Phrases, such as "an embodiment," "one embodiment," among others, used herein, are not necessarily referring to the same embodiment. Features, structures, or characteristics of any embodiment may be combined in any suitable manner with one or more other features, structures, or characteristics.

What is claimed is:

1. A connector comprising:
   a single fluid flow path configured for delivering fluid to a person and configured for receiving fluid from a person;
   an air chamber configured for expelling air from the air chamber when an actuator is inserted into the connector and for receiving air into the chamber when the actuator is removed from the connector; and
   a valve plug comprising two diaphragms that separate the air chamber from the single fluid flow path, wherein the valve plug is configured for creating positive displacement by returning the valve plug to its uncompressed state when the actuator is removed from the connector, and
   wherein the fluid flow path is not required to flow through the valve plug.

2. The connector of claim 1, wherein changes in respective volumes of the fluid flow path and the air chamber due, at least in part, to respective movements of the two diaphragms provide for the positive displacement when the actuator is removed from the connector and provide for negative displacement by compressing the valve plug when the actuator is inserted into the connector.

3. The connector of claim 1, wherein the connector is configured to provide the positive displacement due to a volume associated with the single fluid flow path decreasing and a volume associated with the air chamber increasing when the valve plug returns to the uncompressed state.

4. The connector of claim 1, wherein the connector is configured to provide negative displacement due to a volume associated with the single fluid flow path increasing and a volume associated with the air chamber decreasing when the valve plug is compressed upon insertion of the actuator into the connector.

5. The connector of claim 1, wherein one of the two diaphragms, which is nearer the top of the connector than the other diaphragm, has a larger diameter than the other diaphragm.

6. The connector of claim 1, wherein one of the two diaphragms, which is nearer the bottom of the connector than the other diaphragm, has a larger fluid surface area than the other diaphragm, wherein a fluid surface area is a surface area that interacts with fluid.

7. The connector of claim 1, wherein counter balancing effects of movements of the two diaphragms on a volume of the fluid flow path provides, at least in part, for minimal displacement.

8. The connector of claim 1, wherein an amount of space inside the connector that is occupied by the valve plug provides, at least in part, for minimal displacement.

9. The connector of claim 1, wherein the diaphragms have skirts.

10. The connector of claim 1, wherein the diaphragms have expansions around their edges.

11. The connector of claim 1, wherein the valve plug is made of a single piece of material.

12. A method of making a connector, comprising:
associating a single fluid flow path with the connector, wherein the single fluid flow path is configured for delivering fluid to a person and configured for receiving fluid from a person;
associating an air chamber with the connector, wherein the air chamber is configured for expelling air from the air chamber when an actuator is inserted into the connector and for receiving air into the chamber when the actuator is removed from the connector; and
associating a valve plug, which has two diaphragms, with the connector, wherein the single fluid flow path is not required to flow through the valve plug and wherein the connector provides positive displacement, at least in part, due to a volume associated with the single fluid flow path decreasing and a volume associated with the air chamber increasing, by returning the valve plug and the two diaphragms to an undeformed state upon removal of the actuator from the connector.

13. The method as recited by claim 12, wherein the associating of the valve plug with the connector further comprises:
associating the valve plug with the connector, wherein the connector provides negative displacement due to the volume associated with the single fluid flow path increasing and the volume associated with the air chamber decreasing when the valve plug deforms upon insertion of the actuator into the connector.

14. The method as recited by claim 12, wherein the associating of the valve plug with the connector further comprises:
associating two diaphragms that have skirts with the connector.

15. The method as recited by claim 14, wherein the associating of the two diaphragms that have skirts further comprises:
associating two diaphragms that have skirts, wherein orientation of at least one of the skirts is selected from upwards, downwards, and horizontal.

16. The method as recited by claim 12, wherein the two diaphragms include a top diaphragm and a bottom diaphragm and wherein associating the valve plug with the connector further comprises:
associating the top diaphragm and the bottom diaphragm with the connector, wherein the bottom diaphragm has a smaller diameter than the top diaphragm.

17. The method as recited by claim 12, wherein the two diaphragms have expansions around their respective edges and wherein the associating of the valve plug with the connector further comprises:
associating two diaphragms that have expansions around their respective edges with the connector.

18. The method as recited by claim 12, wherein the two diaphragms include a top diaphragm and a bottom diaphragm and wherein the method further comprises:
sandwiching an expansion at the outer edge of the top diaphragm between an insert and a housing associated with the connector.

19. The method as recited by claim 12, wherein the associating of the valve plug with the connector further comprises:
associating the valve plug that has a shoulder that provides a seal when the shoulder interfaces with an inner wall of a housing for the connector.

20. The method as recited by claim 12, further comprising:
securely connecting an insert with a base that includes a bottom port, wherein the air chamber is provided at least in part by the insert;
inserting the valve plug that includes the two diaphragms into the insert;
placing a housing over the valve plug and the insert, wherein the housing includes a top port, the single fluid flow path flows between the bottom port and the top port, and the two diaphragms separate the air chamber and the single fluid flow path; and
securely connecting the housing to the base.

21. A connector, including:
a housing that includes a top port;
a base that includes a bottom port, wherein the housing is securely connected to the base;
an insert securely connected to the base, wherein the insert is inside a portion of the housing;
an air chamber;
a single fluid flow path that includes the top port and the bottom port; and
a valve plug that includes two diaphragms that separate the air chamber from the single fluid flow path, wherein the valve plug is inside a volume formed by portions of the insert and the housing, wherein the single fluid flow path is not required to flow through the valve plug and wherein the connector is configured to provide positive displacement when the valve plug returns to an undeformed state upon removal of an actuator from the top port.

22. The connector of claim 21, wherein the top of the valve plug and the top of the housing provide a smooth surface.

23. The connector of claim 22, wherein the top of the valve plug provides a seal when respective tops of the valve plug and the housing interact with each other.

24. The connector of claim 21, wherein the valve plug includes a semi-circular notch at least on one side of a throat of the valve plug.

25. The connector of claim 21, wherein the valve plug includes a shoulder that provides a seal when the shoulder interacts with an inner wall of the housing.

26. The connector of claim 21, wherein the valve plug includes a tail and wherein one of the two diaphragms is located at one end of the tail and the other of the two diaphragms is located at the other end of the tail.

27. The connector of claim 26, wherein the tail has at least one curve.

28. The connector of claim 21, wherein one of the two diaphragms has a larger diameter than the other of the two diaphragms.

29. The connector of claim 21, wherein at least one of the two diaphragms has a skirt.

30. The connector of claim 29, wherein the skirt of the at least one skirted diaphragm has an orientation selected from upwards, downwards, and horizontal.

31. The connector of claim 21, wherein at least one of the two diaphragms has an expansion on the outer edge.

32. The connector of claim 21, wherein one of the two diaphragms moves more than the other of the two diaphragms in response to the actuator being inserted into the top port and in response to the actuator being removed from the top port.

33. The connector of claim 21, wherein the air chamber is provided, at least in part, by the insert.

34. The connector of claim 33, wherein the air chamber is formed, at least in part, by the inner walls of the insert, the lower surface of a first of the two diaphragms, the outer surface of a tail of the valve plug, and the upper surface of a second of the two diaphragms.

35. The connector of claim 21, wherein the housing includes a rib that is configured to provide a portion of the fluid flow path.

36. The connector of claim 35, wherein the fluid flow path is formed, at least in part, by inner walls of an upper portion of the housing around a throat of the valve plug, inner walls of the housing around a shoulder of the valve plug, the upper surface of a first of the two diaphragms, the rib of the housing, a lower region of the insert near a second of the two diaphragms, the lower surface of the second diaphragm, and the bottom port of the base.

37. The connector of claim 21, wherein:
   the insert and the base are ultrasonically welded together; and
   the housing and the base are ultrasonically welded together.

* * * * *